United States Patent [19]
Kauker et al.

[11] Patent Number: 5,690,660
[45] Date of Patent: Nov. 25, 1997

[54] ARTHROSCOPIC CUTTER HAVING CURVED ROTATABLE DRIVE

[75] Inventors: Barry J. Kauker, Soquel; Alex L. Lim, San Francisco, both of Calif.

[73] Assignee: Stryker Corporation, Kalamazoo, Mich.

[21] Appl. No.: 626,688

[22] Filed: Apr. 2, 1996

Related U.S. Application Data

[63] Continuation of Ser. No. 433,695, May 3, 1995, abandoned, which is a continuation-in-part of Ser. No. 313,407, Sep. 27, 1991, Pat. No. 5,437,630, which is a continuation of Ser. No. 144,195, Oct. 27, 1993, abandoned.

[51] Int. Cl.⁶ .................................................. A61B 17/32
[52] U.S. Cl. .................... 606/180; 606/170; 604/902; 604/22; 128/752; 128/755
[58] Field of Search ................... 604/22, 902; 606/170, 606/180, 167; 128/751, 752, 753, 754, 755

[56] References Cited

U.S. PATENT DOCUMENTS

| 412,920 | 10/1889 | Reynolds . |
|---|---|---|
| 2,093,682 | 9/1937 | Levy . |
| 3,678,934 | 7/1972 | Warfield et al. . |
| 3,732,858 | 5/1973 | Banko . |
| 3,844,272 | 10/1974 | Banko . |
| 3,882,872 | 5/1975 | Douvas et al. . |
| 3,945,375 | 3/1976 | Banko . |
| 3,990,453 | 11/1976 | Douvas et al. . |
| 3,995,619 | 12/1976 | Glatzer . |
| 3,996,935 | 12/1976 | Banko . |
| 4,014,342 | 3/1977 | Staub et al. . |
| 4,167,944 | 9/1979 | Banko . |
| 4,203,444 | 5/1980 | Bonnell et al. . |
| 4,210,146 | 7/1980 | Banko . |
| 4,246,902 | 1/1981 | Martinez . |
| 4,274,414 | 6/1981 | Johnson et al. . |
| 4,368,734 | 1/1983 | Banko . |
| 4,512,344 | 4/1985 | Barber . |
| 4,517,977 | 5/1985 | Frost . |
| 4,598,710 | 7/1986 | Kleinberg et al. . |
| 4,646,736 | 3/1987 | Auth . |
| 4,646,738 | 3/1987 | Trott . |
| 4,649,919 | 3/1987 | Thimsen et al. . |
| 4,681,541 | 7/1987 | Snaper . |
| 4,811,734 | 3/1989 | McGurk-Burleson et al. . |

(List continued on next page.)

FOREIGN PATENT DOCUMENTS 2 362 157  11/1974  Germany .

OTHER PUBLICATIONS

Figures 1–12 of the present FWC application (formerly U.S. Ser. No. 08/433,695) illustrating an embodiment which is believed to have been publicly available prior to May 3, 1994. (Copies already of record in file).

(List continued on next page.)

*Primary Examiner*—Corrine M. McDermott
*Assistant Examiner*—N. Kent Gring
*Attorney, Agent, or Firm*—Flynn, Thiel, Boutell & Tanis, P.C.

[57] ABSTRACT

A powered rotatable surgical tissue working tool for chucking in a powered rotating surgical handpiece includes a tubular elongate outer member having a distal tip portion angled off the central axis of the proximal portion of such tubular outer member, by reason of a angled portion therebetween. A rotatable elongate inner member extends coaxially and rotatably within the tubular outer member and has a rotatably drivable proximal portion, a distal tip portion for tissue working interaction with the distal tip portion of the outer member, and a flexibly bendable portion therebetween rotatably housed within the angled portion of the outer member. A suction passage communicates between the distal tip portions thereof and the handpiece for permitting suction withdrawal of flowable materials from a surgical site axially through such suction passage and to a suction source. An annular space is maintained between the flexible portion of the inner member and the angled portion of the outer member despite rotation of the inner member.

24 Claims, 10 Drawing Sheets

U.S. PATENT DOCUMENTS

| | | |
|---|---|---|
| 4,819,635 | 4/1989 | Shapiro . |
| 4,834,729 | 5/1989 | Sjostrom . |
| 4,842,578 | 6/1989 | Johnson et al. . |
| 4,923,441 | 5/1990 | Shuler . |
| 4,986,825 | 1/1991 | Bays et al. . |
| 5,007,917 | 4/1991 | Evans . |
| 5,061,238 | 10/1991 | Shuler . |
| 5,152,744 | 10/1992 | Krause et al. . |
| 5,160,318 | 11/1992 | Shuler . |
| 5,192,292 | 3/1993 | Cezana et al. . |
| 5,437,630 | 8/1995 | Daniel et al. .............................. 604/22 |

OTHER PUBLICATIONS

Stryker Brochure 270–70T–11 including Model No. 270–851 entitled "The Elite Arthroscopy Power System".

Baxter Brochure entitled "We've Expanded Our Line So You Can Reduce Yours" 1990 (2 pages).

Smith & Nephew (Dyonics) Brochure entitled "Extending Your Arthroscopic Reach" 1979 (4 pages).

Storz Brochure entitled "Precision Arthroplasty System", No. SPA–1170 (4 pages).

Storz Brochure entitled "Meet the Lightweight Heavyweight Arthro–Ease" (3 pages).

Storz Brochure entitled "The Large Joint and Microarthroplasty System . . ." (2 pages–with attached 2 page price list).

Storz Brochure entitled "We Know the Importance of Staying Sharp!", No. 1188–2500–A115 (2 pages).

Baxter Brochure entitled "The Powercut ™ Surgical System", No. 104–01–880–ORTHO (3 pages).

Dyonics Brochure entitled "Dyonics Disposable Blades are the Right Tools", 1989, No. P/N 1060112 (3 pages).

Concept Brochure entitled "Intra–Arc ® Drive System", No. 812388 (4 pages).

Zimmer Brochure entitled "Big on Performance", No. 97–3000–324 (4 pages).

Bowen Brochure entitled "Advances in Arthroscopy" (4 pages) and photo A and sketch B showing the Bowen angle–headed rotary cutter.

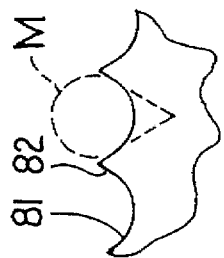
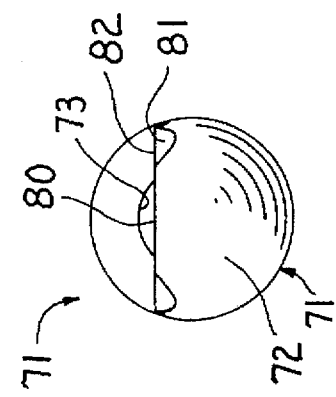
FIG. 7
FIG. 6
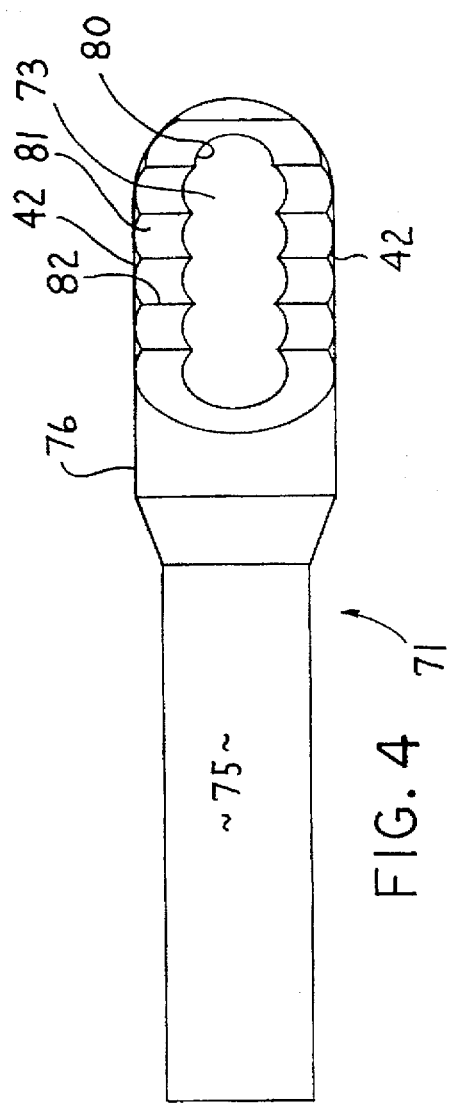
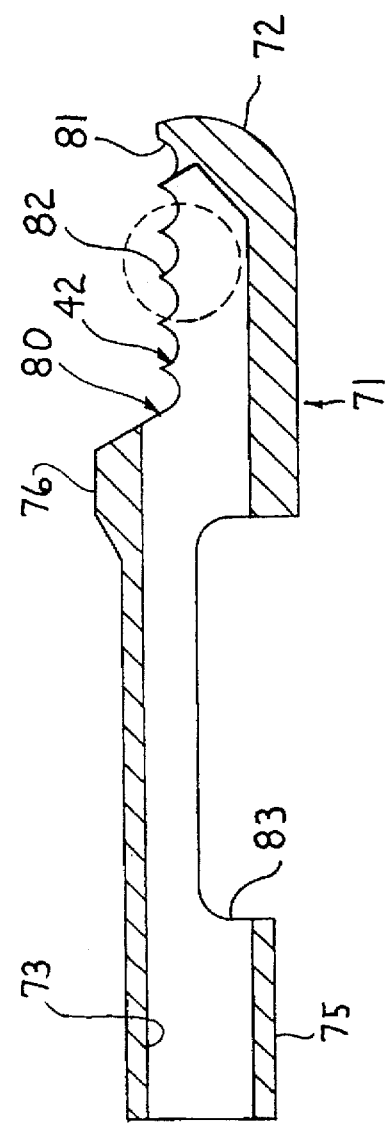
FIG. 4
FIG. 5

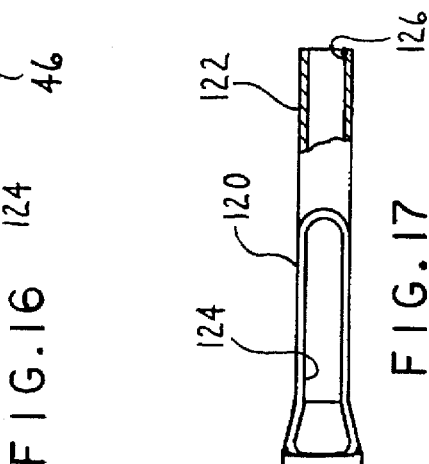
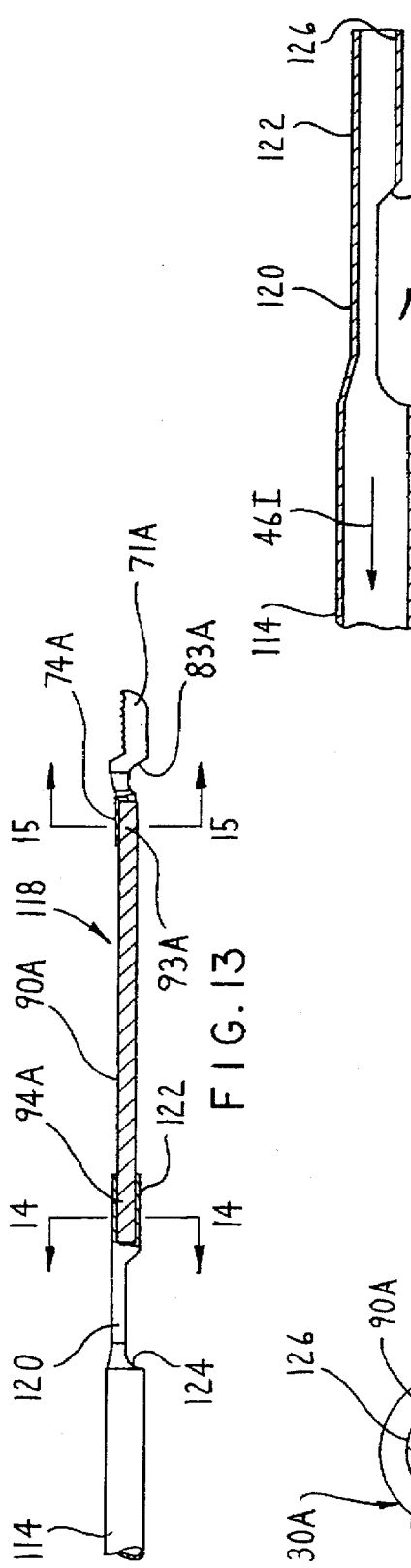
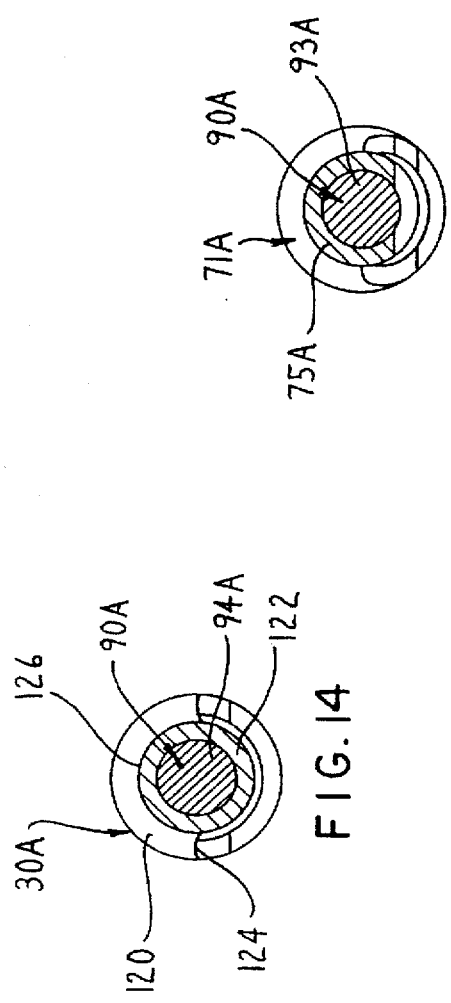

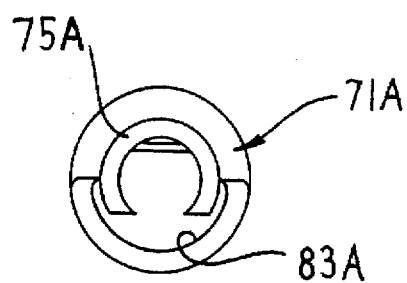
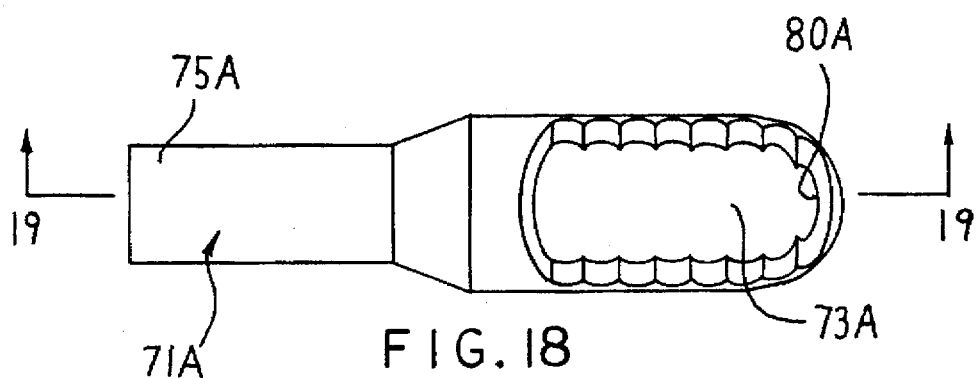
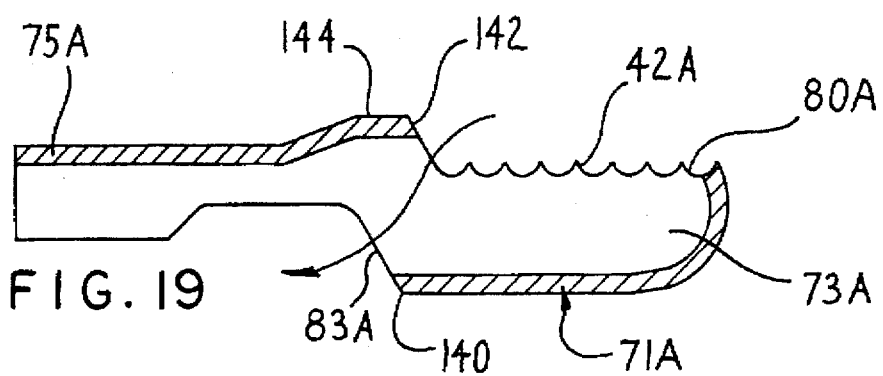
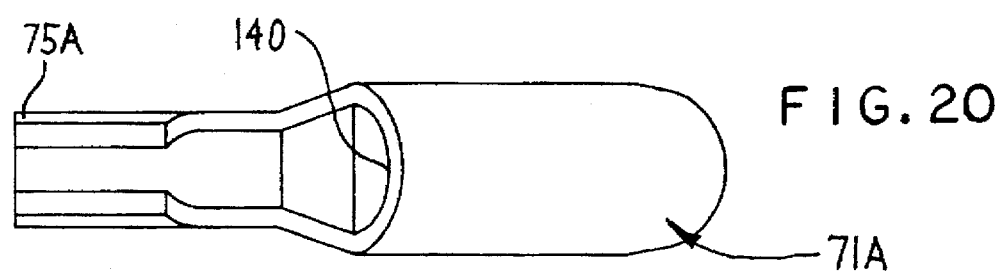

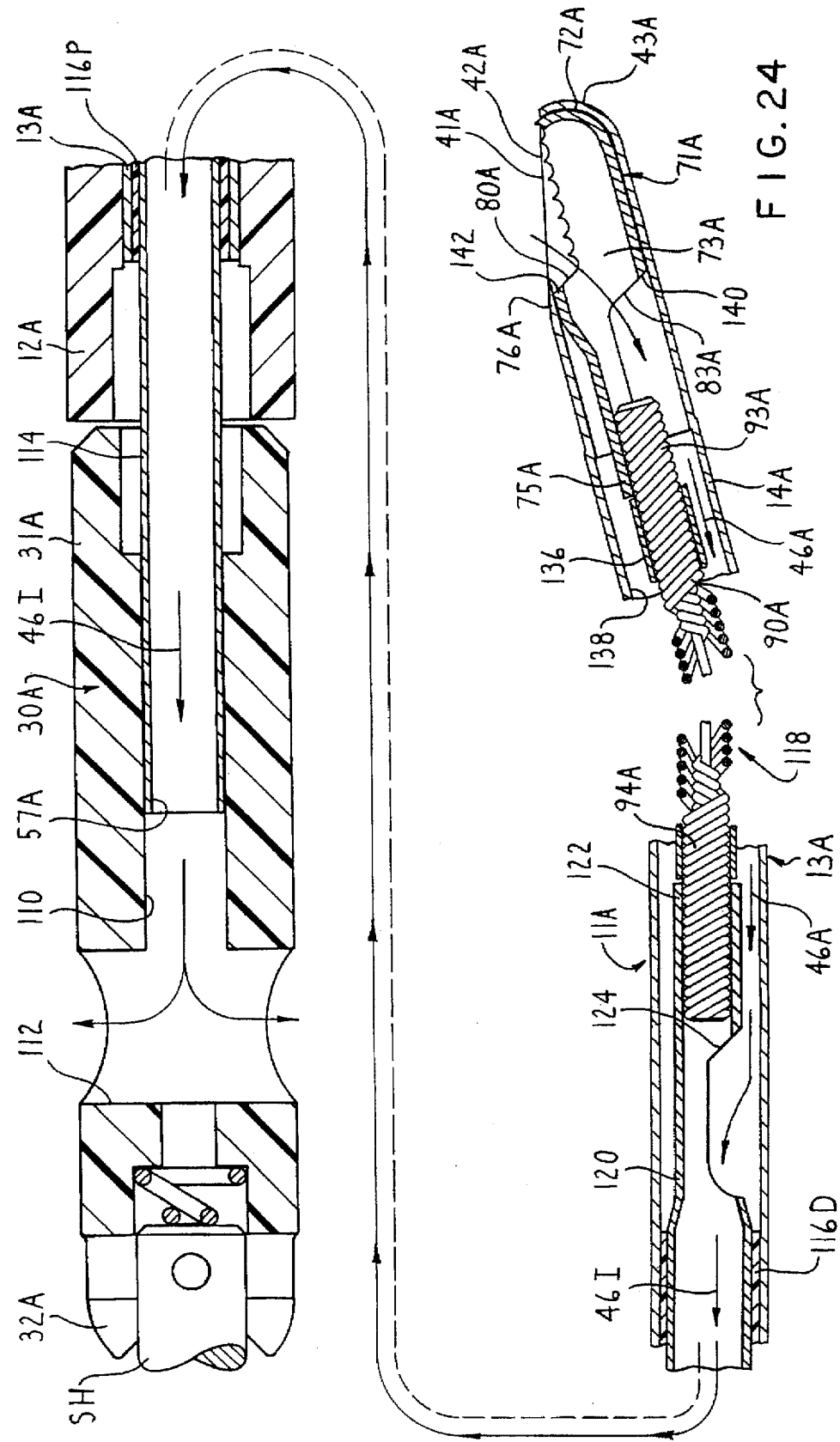

ARTHROSCOPIC CUTTER HAVING CURVED ROTATABLE DRIVE

CROSS REFERENCE TO RELATED APPLICATIONS

This application is a continuation application of U.S. patent application Ser. No. 08/433 695, filed on May 3, 1995 now abandoned, which is a continuation-in-part application of U.S. patent application Ser. No. 08/313 407, filed on Sep. 27, 1994 now U.S. Pat. No. 5,437,630, which is a continuation application of U.S. patent application Ser. No. 08/144 195, filed on Oct. 27, 1993, now abandoned.

FIELD OF THE INVENTION

This invention relates to a rotatable surgical tool drivable by a powered rotary surgical handpiece and useable for arthroscopic surgery.

BACKGROUND OF THE INVENTION

U.S. Pat. No. 5,192,292 (Cezana et al), assigned to the Assignee of the present invention, discloses a straight, or linear, rotatable arthroscopic tool and a powered rotary surgical handpiece for releasably chucking and rotatably driving such tool. The tool comprises a tubular outer member having a hollow base at its proximal end for releasably fixed chucking on the handpiece, an elongate, slim, tubular intermediate portion, or sleeve, fixedly extending forward from said base and having a distal tip portion terminating the distal end of the sleeve. The tool further comprises a rotatable inner member having a proximal end portion defining a hub for rotational driving by a rotor of the handpiece when the tool is chucked in the handpiece. The rotatable inner member further comprises an intermediate portion extending forward from and rotatable in fixed relation with the hub and ending in a distal tip portion. The hub protrudes rearwardly from the tubular outer member, whereas the intermediate portion and distal tip portion of the rotatable inner member are sleeved within the tubular outer member. The distal tip portion of the rotatable inner member lies within and is rotatable within the distal tip portion of the tubular outer member. The distal tip portions are provided with means for surgically working tissue of a patient at a surgical site on the patient. The tissue working means may for example, comprise coacting oval shearing slots, or windows, on the distal tip portions. In one unit according to the aforementioned patent, a toothed shearing edge on the inner member slot coacts in a shearing fashion with a cutting edge on the outer member slot.

In the tool disclosed in the aforementioned U.S. Pat. No. 5,192,292, the rotatable inner member is tubular and open from the distal tip portion thereof through the intermediate portion and to a location on the hub in communication through the handpiece with a suction source, for suctioning flowable material, including irrigation liquid and pieces of tissue, from the surgical site.

In this prior patented device, the hollow tubular inner member is snugly, though rotatably, supported within the tubular outer member such that the flow of suctioned flowable material from the surgical site to the handpiece is inside the hollow tubular inner member. Further, the inner and tubular outer member are substantially rigid so that both are necessarily straight, to allow rotation of the inner member within the outer member.

The present assignee, Stryker Corporation, under model designation 270-851, has for several years manufactured a tool generally similar to that described above but wherein the above-mentioned coacting shearing slots are absent. The rotatable inner member carries a burr at its distal end exposed through the open front and of the outer tubular member, and the inner rotatable member has a solid shaft of maximum diameter substantially less than the interior diameter of the outer tubular member so as to provide an annular clearance therebetween. The intermediate portion of the inner shaft is supported by several axially spaced bushings distributed along its length and supported by the interior wall of the outer tubular member. Such bushings are provided with axially extended grooves which are open radially and endwise to allow suction of flowable materials from the surgical site along the length of the tool to the handpiece radially between the shaft and the inner wall of the outer tubular member. Again, the outer tube and inner shaft are both rigid and are thus necessarily straight to allow relative rotation.

U.S. Pat. No. 5,152,744 (Krause et al), assigned to Smith and Nephew Dyonics, discloses a tool in which the rigid outer tubular member is curved near its distal end, so that the distal end is angled from the intermediate portion of the tool. The rotatable inner member is a hollow tubular member closely rotatably supported for rotation within the outer tubular member. The inner tubular member, adjacent its distal end, and in the curved portion of the outer tubular member, is purportedly made flexible enough to rotate within the curved outer tube in several alternative ways. In one embodiment, Krause reduces the diameter of the purportedly flexible portion and perforates it with closely axially and circumferentially spaced holes. Alternatively, Krause makes this portion purportedly flexible enough to rotate within the curved outer tube, by cutting therein axially and circumferentially close spaced, circumferentially extending, elongate chordal slots, the slots being connected by narrow circumferential and axial webs. The slots each extend almost halfway through the diameter of the inner tube. Axially adjacent pairs of these chordal slots are angularly shifted through 90° with respect to each other. In a further embodiment, the purported flexibility sufficient to enable rotation of the inner tube within the curved portion of the outer tube is to be achieved axially close spaced, radially planar slots cut almost all the way through the thickness of the inner tubular member, leaving only a narrow web of axially extending tube material between the circumferential ends of each slot, and wherein axially alternate slots open in diametrically opposite directions, the slots each being filled and hence closed with a web of silicone rubber to prevent leakage of flowable material radially out of the flexible portion of the rotatable inner tube.

U.S. Pat. No. 4,646,738 (Trott), assigned to Concept, Inc., rather similarly discloses a curved tubular outer member snugly rotatably supporting therein a hollow tubular inner member. The latter has a purportedly flexible portion in the curved zone of the tubular outer member, and comprising a set of three spirally wound tubes of flat metallic ribbon which are disposed one within the other to provide inner, middle and outer spirally wound tubes. The inner, middle and outer spirals are wound in alternating opposite directions and are spot welded at each end to form a composite three-layer purportedly flexible tube. Torque applied to one end of such composite flexible tube is to be transmitted by alternate layers trying to expand (unwind) or trying to contract (wind up) such that the middle spiral is to either attempt to expand and be resisted by contraction of the outer layer or the middle spiral is to attempt to contract or wind up and be resisted by the inner spiral. Further, the three spirals are welded to each other by spot welds disposed longitudinally along the spirally wound composite tube.

Accordingly, the objects and purposes of the present invention include provision of a tool drivable by a powered rotative surgical handpiece, wherein the tool has a fixed outer tubular member with an angled portion near the distal end thereof and inner rotatable member with a flexible portion at the angled portion of the outer member, in which such tool overcomes apparent difficulties of the prior art, including avoiding excessive friction between angled, snugly radially telescoped inner and outer tubes during rotation of the inner tube, high torque and power expenditures, excessive heating, friction and heat induced fatigue or wear, cost and complexity and unreliability of manufacture of hollow flexible tube portions, possible migration of hard (e.g. bone) fragments into flexible inner rotor slots (which may impede closing thereof and hence flexing) and through such slots into a close clearance rotative interface between inner and outer members so as to upset rotating clearances therebetween, inability to withdraw the inner member rearwardly out of the outer member and replace same forwardly into the outer member, and the like.

SUMMARY OF THE INVENTION

A powered rotatable surgical tissue working tool, for chucking in a powered rotating surgical handpiece. The tool includes a tubular elongate outer member having a distal tip portion angled off the central axis of the proximal portion of such tubular outer member, by reason of an angled portion therebetween. A rotatable elongate inner member extends coaxially and rotatably within the tubular outer member and has a rotatably drivable proximal portion, a distal tip portion for tissue working interaction with the distal tip portion of the outer member, and a flexibly bendable portion therebetween rotatably housed within the angled portion of the outer member.

An annular space between the inner and outer member communicates from the distal tip portions thereof to the handpiece for permitting suction withdrawal of flowable materials from a surgical site axially through such annular space and to a suction source. The annular space is maintained between the flexible portion of the inner member and the angled portion of the outer member despite rotation of the inner member.

In a further embodiment of the invention, the proximal portion of the elongate inner member is formed as a hollow tube which defines an interior suction passage, the flexibly bendable portion is connected to a transition portion of the proximal portion wherein the transition portion includes an opening which communicates in one direction with the interior suction passage of the proximal portion and in the opposite direction with the annular suction passage disposed about the flexibly bendable portion. This arrangement further facilitates the free flow of removed tissue along the axial length of the rotatable elongate inner member. In addition, the head includes additional features which also facilitate the free flow of tissue through the head.

Other objects and purposes of the invention will be apparent to those familiar with apparatus of this general kind upon reading the following specification and inspecting the accompanying drawings.

BRIEF DESCRIPTION OF THE DRAWINGS

FIG. 4 is an enlarged plan view of a preferred rotatable inner member head of the tool of FIGS. 1–3.

FIG. 5 is a central cross sectional view substantially taken on the line 5—5 of FIG. 4.

FIG. 6 is a distal end view of the FIG. 4 head.

FIG. 7 is a fragment of FIG. 5 showing a preferred tooth form.

FIG. 13 is a side view in partial section of a further embodiment of the tool embodying the invention.

FIG. 14 is an enlarged sectional view substantially taken on the line 14—14 of FIG. 13.

FIG. 15 is an enlarged sectional view substantially taken on the line 15—15 of FIG. 13.

FIG. 16 is an enlarged fragmentary view of FIG. 13 with the rotatable inner member shown in central cross section.

FIG. 17 is an enlarged fragmentary bottom view of FIG. 13 with the rotatable inner member shown in partial cross section.

FIG. 18 is an enlarged plan view of the further embodiment of the rotatable inner member head of the tool of FIG. 13.

FIG. 19 is a central cross sectional view substantially taken on the line 19—19 of FIG. 18.

FIG. 20 is a bottom view of the head illustrated in FIGS. 18 and 19.

FIG. 21 is a proximal end view of the head illustrated in FIGS. 18–20.

FIG. 24 is an enlarged fragmentary central cross sectional view of the tool of FIGS. 13–22 and showing schematically the flow paths of the tool.

DETAILED DESCRIPTION OF THE INVENTION

Figure 1:
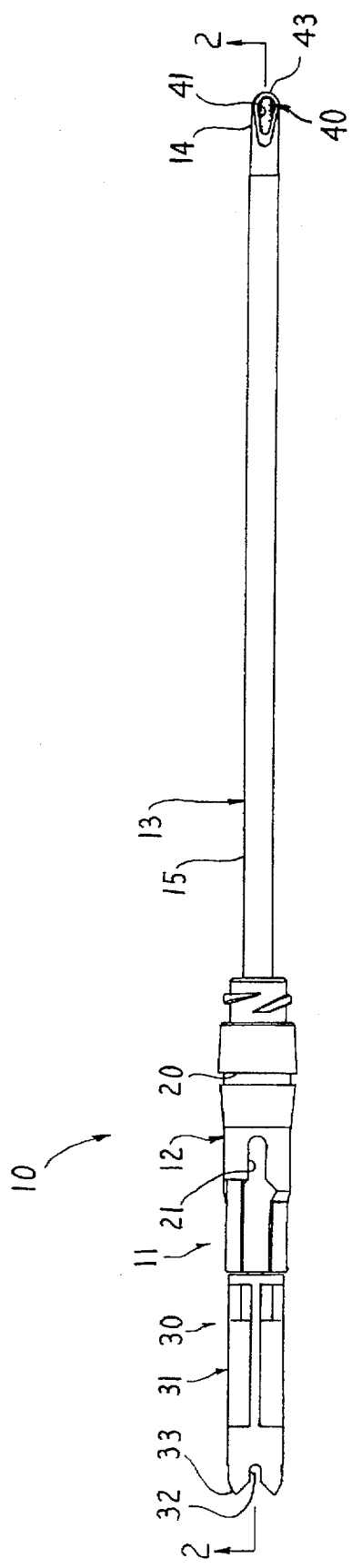
FIG. 1 is a top view of a tool embodying the invention.

A tool 10 (FIGS. 1 and 2) embodying the invention is adapted for chucking in a powered rotating surgical handpiece of any desired kind, an example which is disclosed in above-mentioned Cezana et al U.S. Pat. No. 5,192,292, (assigned to the assignee of the present invention). Such a handpiece is schematically indicated at HP in FIG. 2. The handpiece HP has a housing H fixedly containing a suitable rotary drive motor means, indicated in broken lines at MM (for example electrically or fluid powered). The motor means MM has a rotary output shaft SH extending forward therefrom and fixedly carrying at its front end a diametrically protruding drive pin DP (FIG. 2). Although the handpiece HP may contain a suitable power source, such as electric batteries, in the example shown, same is connectible to a suitable remote power source P, for example electrical power source or a pressure gas source. The handpiece HP also preferably includes a connection to a suitable suction source S.

The tool 10 comprises a tubular outer member 11 (FIG. 2) comprising a proximal hollow base 12. An elongate tubular sleeve 13 is fixedly telescoped in and extends coaxially forwardly from the hollow base 12. The sleeve 13 includes a distal tip portion 14 and an intermediate portion 15 extending from the base 12 toward the distal tip portion 14. The sleeve 13 is here a rigid, thin walled, constant diameter, circular cross-section tube of stainless steel or equivalent material. The base 12 is configured to be rearwardly insertable in, fixedly held by, and releasably removable forward from a chuck C on the forward end of the handpiece HP. To cooperate with the chuck of the handpiece shown in above-mentioned U.S. Pat. No. 5,192,292, the base 12 (FIGS. 1 and 2) includes on its surface an annular groove 20 forward of a rearwardly opening, generally funnel shaped slot 21. Upon rearward insertion of the tool 10 into the handpiece HP (rearward insertion of the base 12 into the chuck C) of U.S. Pat. No. 5,192,292, the base slot 21 receives a radially inward extending fixed pin in the chuck C, which fixes the outer member 11 against rotation in the handpiece HP. Simultaneously, the annular groove 20 in the outer member base 21 receives diametrically opposed half rings 23 in the chuck. The half rings are diametrically biased toward each other by spring means 24 in the chuck C, as schematically indicated in FIG. 2, to axially fix the outer member base 21 with respect to the handpiece HP. The handpiece HP includes means, not shown, manually actuable to pull apart the half rings 23 to thereby allow tool 10 to be pulled forwardly out of the handpiece chuck C after surgery, or during surgery when it is desired to substitute a different tool into driving relationship with the handpiece HP.

Figure 2:
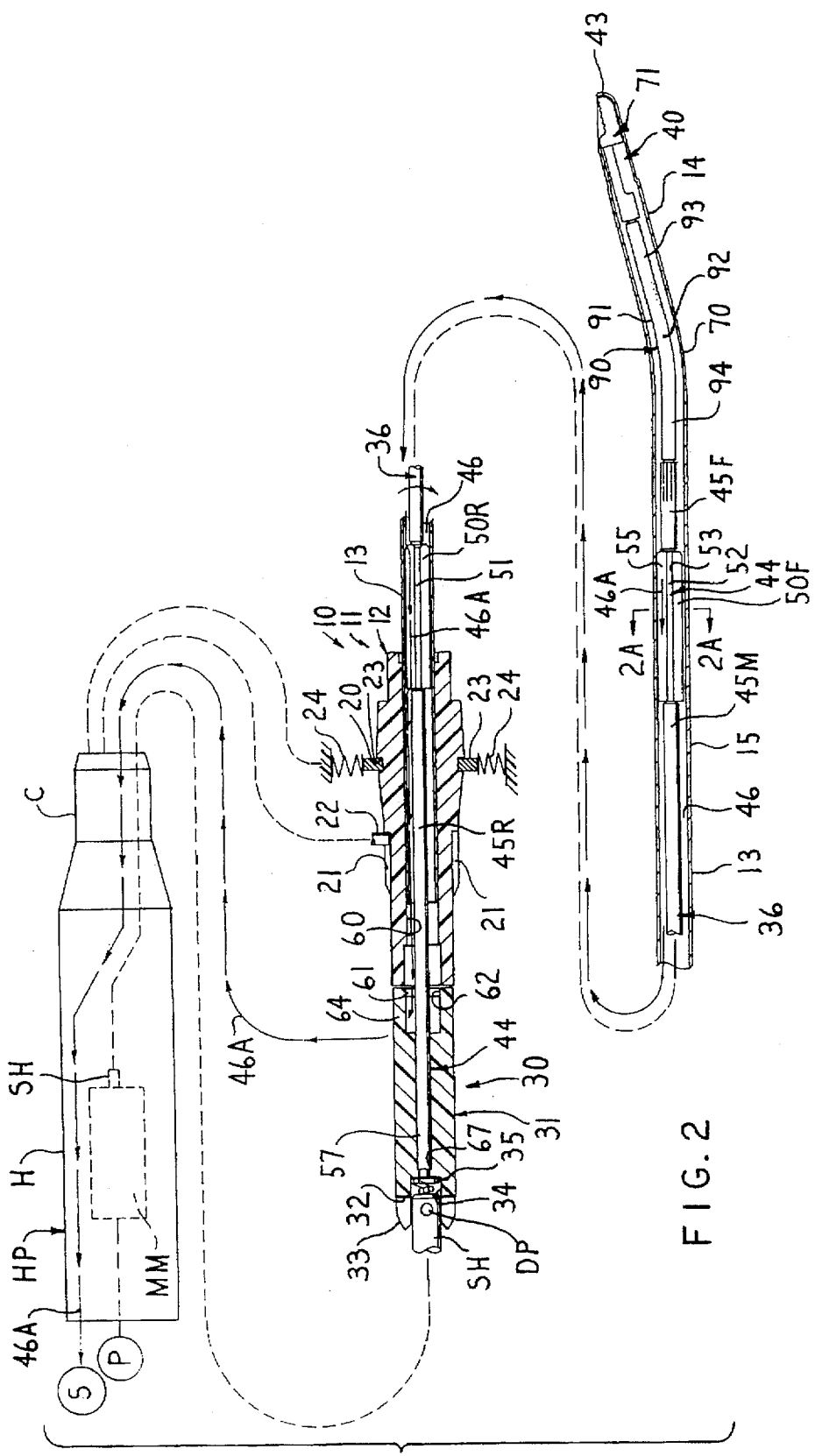
FIG. 2 is an enlarged fragmentary central cross sectional view substantially taken on the line 2—2 of FIG. 1 and showing schematically the cooperating parts of a corresponding handpiece.

A driven rotatable elongate inner member 30 extends coaxially and rotatably within the tubular outer member 11 (FIGS. 1 and 2). The rotatable inner member 30 has a proximal end portion, defining a hub 31 rotatably drivably engageable by the rotary handpiece shaft SH and its transverse drive pin DP. More particularly, in the embodiment shown, the hub 31 includes at least two (here four) diametrically opposed, evenly circumferentially distributed, rearward opening notches 32 circumferentially spaced by a corresponding number of rear extending fingers 33. The notches 32 and fingers 33 surround and extend rearward from a central, blind, rear opening recess 34 (FIG. 2) in the hub 31. A coil compression spring 35 (FIG. 2) is snugly housed in the recess 34 and extends rearward therefrom.

The rotatable inner member 30 has an intermediate portion 36 (FIG. 2) coaxially fixed to and extending forward from the hub 31. The rotatable intermediate portion 36 is supported for rotation within the intermediate portion 15 of the tubular outer member 11 in a manner hereafter discussed. The rotatable inner member 30 has a distal tip portion 40 fixed forward of the intermediate portion 36 for rotation therewith and snugly rotatably disposed within the distal tip portion 14 of the tubular outer member 11.

The distal tip portions 14 and 40 here have means, hereafter discussed more fully, for surgically working the tissue of a patient at a surgical site on the patient. Tools of the herein described type can be provided with a variety of different purpose surgical tissue working means including burrs, cutters, etc. of conventional type. In the FIGS. 1 and 2 example, the distal tip portion 14 of the outer tubular member 11 is provided with an angled, laterally and somewhat forwardly opening, planar window 41. The window 41 has laterally opposed cutting edges. The window 41 may be so formed by forming the distal tip portion of the tubular outer member with a semi-spherical closed end and then machining away a part thereof in an angled planar manner as here shown in FIGS. 1 and 2. The inner distal tip 40 is rotatable snugly within the outer distal tip portion 14 and has a cutting edge 42 rotatable in shearing relation past the cutting edge of the window 41.

The inner member 30 is axially insertable forwardly into the tubular outer member 11 and is axially rearwardly removable therefrom when not installed on a handpiece HP. On the other hand, when installed on a handpiece HP, by rearward insertion into the forward extending chuck C thereof, the forward end of the shaft SH of the handpiece partly compresses the spring 35 (FIG. 2) of the inner member hub 31, to push the inner distal tip portion 40 forward snugly against the front end 43 of the distal tip portion 14 of the outer member 11, so as to axially accurately position the rotatable inner tip portion 40 with respect to the outer tip portion 14. This properly aligns the cutting edge of the outer member window 41 with the rotary cutting edge 42 of the inner distal tip portion 40 and maintains the proper relative axial position therebetween during cutting. Also with the tool 11 installed in the handpiece HP, the diametrical drive pin DP of the handpiece shaft enters and rides in a diametrically opposed pair of the notches 32 of the hub 31 and, upon rotation of the shaft SH, the drive pin DP correspondingly rotates the inner rotatable member 30 and thereby rotates the distal tip portion 40 thereof to rotationally move its cutting edge 42 past the corresponding cutting edges of the outer member window 41.

In various surgical procedures, for example in trimming the edge of the meniscus cartilage in knee surgery, it is often desirable to irrigate with liquid the surgical site (in a conventional manner not shown) and then to draw by suction flowable material (irrigation liquid, bits of removed tissue, etc.) from the surgical site. This can be done by drawing such flowable material into the window 41, then rearwardly along the length of the outer member 11 and further rearwardly through a portion of the hub 31 and then radially outwardly into a suction path through the handpiece and outward therefrom to the suction source S. Thus, the tool 10 can be used for simultaneously cutting tissue at the surgical site and removing flowable material from the surgical site.

To the extent above described, the tool 10 is conventional and one example thereof is shown in above-referenced Cezana et al U.S. Pat. No. 5,192,292.

Unlike in such patent, the intermediate portion 36 of the rotatable inner member 30 comprises a rigid, solid (not hollow) shaft 44 having coaxial front, mid and rear parts 45F, 45M, and 45R of elongate cylindrical form and of diameter sufficiently less than the inside diameter of the sleeve 13 as to create an annular suction passage 46 between the shaft 44 and inside of the sleeve 13 for drawing of flowable materials from a surgical site. The suction passage 46 runs the length of the tool from the distal tip portion 14 of the tubular outer member 11 rearward through the base 12 into the front end of the hub 31 and radially outward therefrom (as hereafter detailed) and through a portion of the handpiece HP indicated by the arrows 46A to the conventional suction source S. In the embodiment shown, the outside diameter of the shaft parts 45F, 45M, and 45R is about ⅔ the inside diameter of the sleeve 13, leaving a substantial radial clearance therebetween for suction of fluid materials from the surgical site.

To rotatably support the shaft for coaxial rotation within the sleeve 13, axially elongate front and rear bushings 50F and 50R respectively are disposed rotatably on reduced diameter parts 51 and 52 of the shaft 44 between the axially spaced shaft parts 45R, 45M and 45R. The shaft parts 51 and 52 are elongate and cylindrical but of diameter less than the shaft parts 45F, 45M and 45R.

Figure 2A:
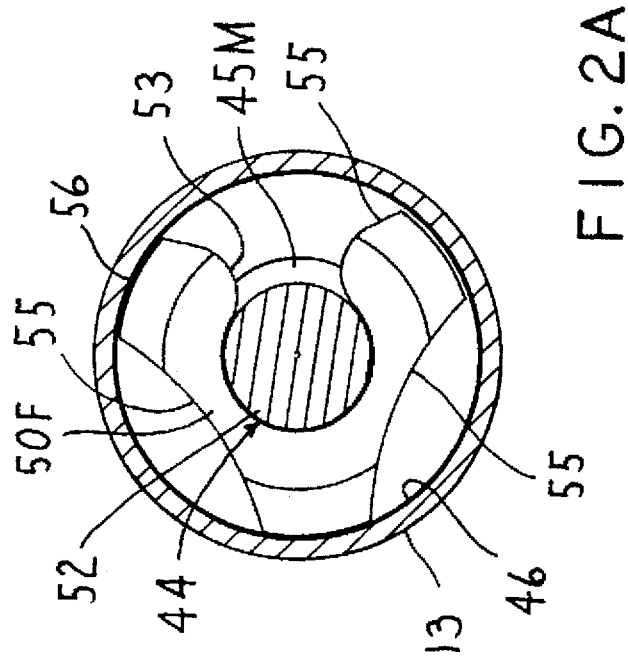
FIG. 2A is an enlarged sectional view taken substantially on the line 2A—2A of FIG. 2.

To allow the portions 45F, 45M and 45R to be of diameter larger than the shaft parts 51 and 52, the bushings 50 F and R are constructed to snap radially onto the corresponding reduced diameter shaft parts 51 and 52. The bushing 50F applied to the shaft part 52 is shown in FIG. 2A, it being understood that the shaft part 51 and rear bushing 50 are preferably identical. To admit the shaft part 51, 52 radially thereinto, each bushing 50F, R has a slot 53 running axially the length thereof and opening radially outward to the interior of the sleeve 13 and inward to a coaxial, circular cross section bore 54 which extends the length thereof and rotatably coaxially supports the corresponding reduced diameter portion 51 or 52 of the shaft 44. The narrowest width of the slot 53 is slightly more than the outside diameter of the corresponding reduced diameter shaft part 51, 52, permitting the bushing to flex circumferentially enough to widen the slot 53 and allow radial snapping of the bushing over the shaft into the coaxially centered relation shown in FIG. 2A.

In addition, the bushings 50F, R have circumferentially distributed channels 55 indenting the perimeter thereof for the length thereof, one of the channels 55 constituting a funnel-like circumferential widening of the slot 53. The channels 55 continue the suction flow passage 46 axially along and past the bushings 50F, R. Preferably the bushings 50F, R each have three circumferentially distributed channels 55, leaving therebetween three evenly circumferentially spaced, radially outwardly extending lobes 56 (FIG. 2A) radially sized and circumferentially shaped to slide, with the shaft, axially forwardly into the sleeve 13 to the location shown in FIG. 2, for rotatably supporting the shaft with respect hereto. The bushings 50F, R are substantially coextensive in length with the corresponding reduced diameter shaft parts 51, 52. The bushings 50F, R are thus axially snugly sandwiched between the shaft front, mid and rear parts 45F, M, R. The bushings 50F, R are preferably of low friction molded plastics material, such as polycarbonate (in one unit partially glass fiber (30%) filled polycarbonate).

The shaft 44 further includes a drive end portion 57 (FIG. 2) which extends coaxially and integrally fixedly rearwardly from the rear shaft part 45R and rearward coaxially beyond the rear end of the hollow base 12 and is coaxially fixed in driven relation in the hub 31. The base 12 and hub 31 are preferably of rigid molded plastics material, such as polycarbonate. The base 12 and hub 31 are conventionally fixed coaxially as by molding on the rear end portions of the sleeve 13 and shaft 44 respectively. The sleeve 13 and shaft 44 are preferably of rigid stainless steel.

Figure 12:
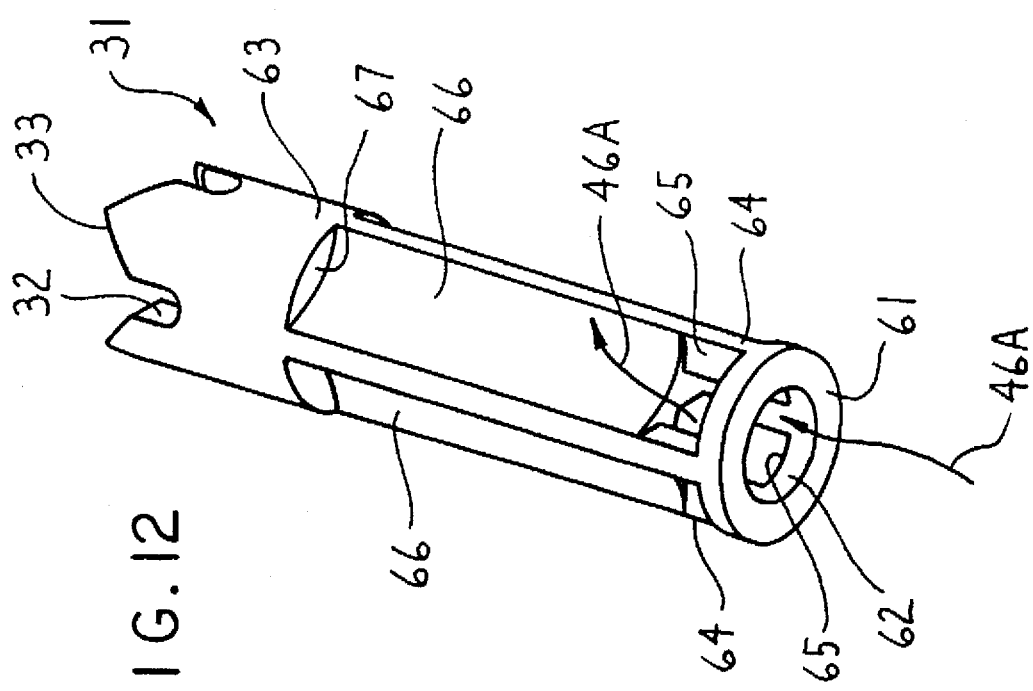
FIG. 12 is a pictorial view of the rotatable drive hub of the FIG. 1 tool.
Figure 3A:
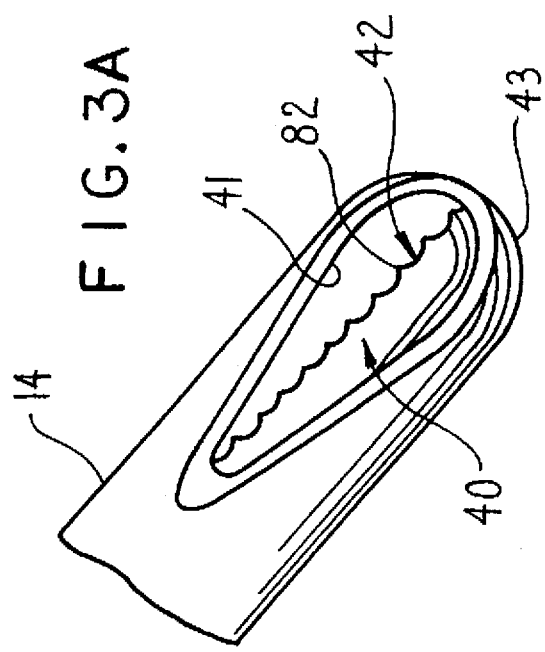
FIG. 3A is a fragmentary pictorial view of the angled distal tip portion of the FIGS. 1–3 tool.

The hub 31 (FIG. 12) is formed to receive flowable material from the surgical site, and more immediately from the central bore 60 (FIG. 2), and to pass it to the surrounding portion of the handpiece HP for transfer through the suction passage (not shown) in the handpiece to the suction source S. To this end, the front end of the hub 31 defines a ring 61 having a central opening 62 for loosely coaxially receiving therethrough the shaft driven end portion 57 (FIG. 2). The main body 63 (FIG. 12) of the hub 31 is axially spaced from the ring 61 by circumferentially spaced columns 64 defining open windows 65 circumferentially therebetween. The windows 65 open radially outward and also open rearward into corresponding rearwardly extending, correspondingly circumferentially spaced, troughs 66, which end blindly at 67, in spaced relation ahead of the notches 32. Thus, suctioned flowable material from the surgical site passes rearwardly from the central bore 60 of the base 12 (FIG. 2), along the shaft driven end portion 57, through the central opening 62 and more particularly through the annular space between the ring 61 and shaft driven end portion 57, into the flow direction changing space bounded by the columns 64. There the flow is diverted radially outward and rearwardly to flow into the troughs 66 and the portion of the handpiece HP surrounding same, so as to thereafter pass out of the handpiece HP through the suction passage therein (not shown), in the direction of the arrows 46A, to the conventional suction source S.

Figure 8:
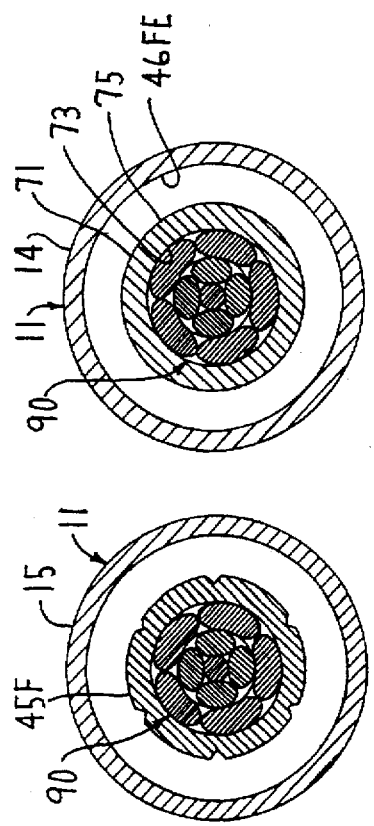
FIG. 8 is a sectional view substantially taken on the line 8—8 of FIG. 3.

It will be noted that the shaft rearward driven end portion 57 continues rearward into the main body 63 of the hub 31 (FIG. 2) and abuts a step 68 (FIG. 8) which faces forward from a location adjacent the rear opening recess 34 so that forward pressure on the hub 31 exerts a similar forward pressure against the shaft 44.

Turning now more particularly to aspects of the tool 10 embodying the present invention, attention is directed to FIG. 2.

Under the present invention the distal tip portion 14 (FIG. 2) of the tubular outer member 11 is angled, here at about 15°, with respect to the intermediate portion 15 of the sleeve 13, by reason of an angled portion 70 of the sleeve. The angled portion 70 is smoothly curved as seen in FIG. 2 and the interior of the sleeve maintains its normal circular cross section and diameter from the intermediate portion 15, through the angled portion 70, and into the distal end portion 14. The smooth curvature of the angled portion 70 is achieved by drawing its central length axis arc on a relatively long radius, for example 6 to 8 times the outside diameter of the sleeve 13.

Figure 3:
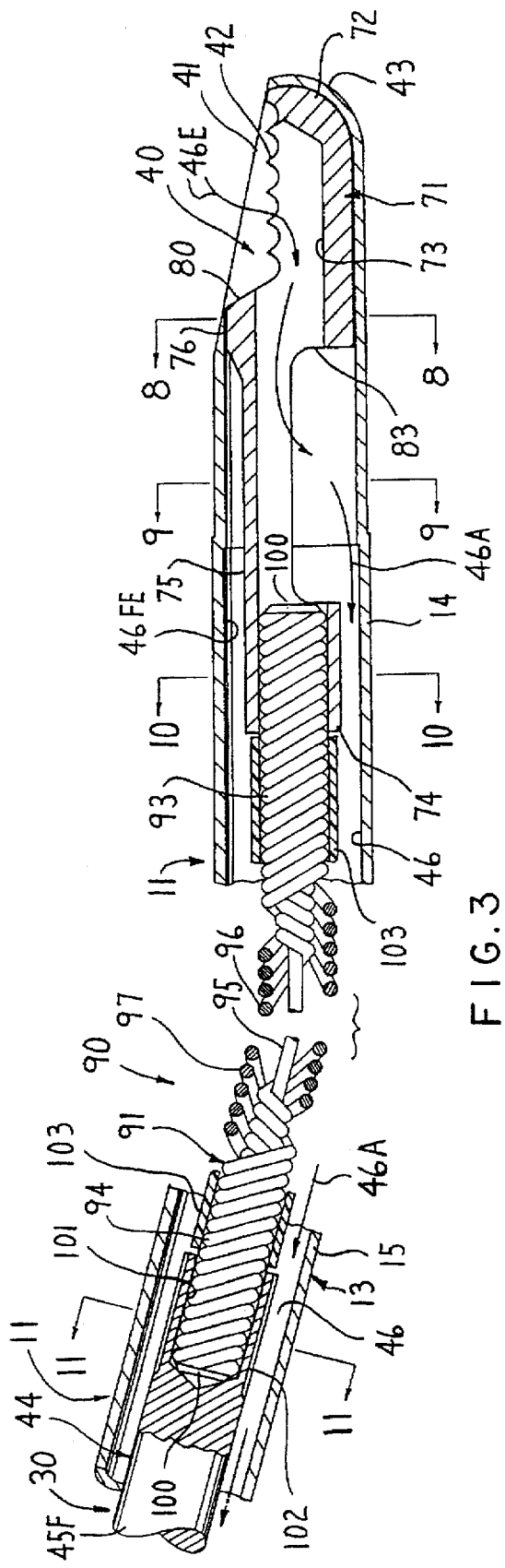
FIG. 3 is an enlarged fragment of FIG. 2 with the rotatable inner member shown in central cross section.
Figure 10:
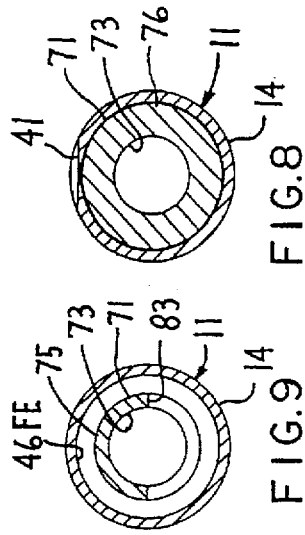
FIG. 10 is an enlarged sectional view substantially taken on the line 10—10 of FIG. 3.
Figure 11:
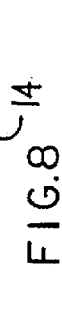
FIG. 11 is an enlarged sectional view substantially taken on the line 11—11 of FIG. 3.
Figure 9:
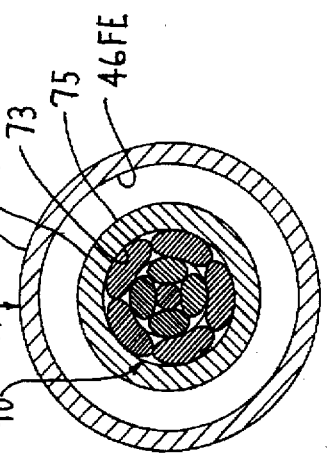
FIG. 9 is a sectional view substantially taken on the line 9—9 of FIG. 3.

The distal tip portion 40 (FIGS. 2 and 3) of the inner rotatable member 30 comprises a tissue working head 71. The head 71 has a substantially modified bullet shape and indeed can be conveniently manufactured from a bullet shaped blank. The head 71 has a convexly rounded nose 72 which snugly rotates within and bears axially forward on the inner face of the convexly rounded front end 43 of the distal tip portion 14 of the tubular outer member 11. The nose 72 and front end 43 are both preferably hemispherical, as shown. A central bore 73 is a conveniently drilled coaxially in the rear end 74 of the head 71 and extends coaxially forward to the nose 72 (FIG. 3). The central bore 73 extends forward from the head rear end 74. Approximately ⅗ of the length of the head 71 is radially relieved to provide a reduced outside diameter and wall thickness, cylindrical, substantially tubular tail 75. The tail 75 has about the same outer diameter as the shaft portion 45F and is thus radially surrounded by an annular front extension 46FE of the suction passage 46. The head 71 is thus left with a forward radial bearing portion 76, ahead of the front end of the tail 75, namely ahead of the forward extension 46FE of the suction passage and behind the window 41 in the tubular outer member 11. This bearing portion 76 coaxially rotatably supports the head 71 within the distal tip portion 14 of the tubular outer member 11.

To define the cutting edge 42 of the inner rotatable member 30, a circumferential portion (the upper circumferential portion with the head oriented rotatably as shown in FIG. 3) is removed in any convenient way, for example by milling with a relatively small diameter milling cutter of circular cylindrical shape generally indicated in dotted lines at M in FIG. 7. Thus, as indicated in more detail in FIGS. 4–6, successive applications of the milling cutter M here leave an upward opening mouth 80 in relatively large area communication with the central bore 73 of the head 71. In the embodiment shown, the mouth is thus defined by a series of upwardly concave, transversely extending, semi-circular cross section grooves 81 arranged side by side along a substantially chordal plane from the rearward end to the forward end of the mouth 80 and defining the transversely opposed pair of cutting edges 42 on transversely opposite sides of the mouth 80 which in profile, as seen in FIG. 5, provide an appearance of a series of teeth 82. Although the mouth 80 here shown is structured to effectively cooperate its cutting edges 42 in an efficient shearing manner with the adjacent edges of the window 41 of the tubular outer member 11, it will be understood that other types of tissue working cooperation, and structure therefore, may be provided in place of the particular window 41 and mouth 80 here shown. However, the head 71 provides a path for fluent material, including bits of tissue and the like, to be drawn from the surgical site outside the distal portion 14 of the outer tubular member 11 and into the central bore 73 of the head 71, as generally indicated by the further arrows 46E entering the central bore 73 through the window 41 and mouth 80 in FIG. 3, from the surgical site.

A transverse, chordal (here substantially diametral) flow port 83 (FIG. 3) is formed (preferably milled) in the forward end of the tubular tail 75. The port 83 is here about the same axial length as the nose portion of the head extending forward therefrom, and about twice the axial length of the residual portion of the tail 75 extending rearward therefrom. The flow port 83 provides large area communication with the central bore 73. Thus, the port 83 allows relatively free flow of flowable materials therethrough from the mouth 80 rearwardly and radially outwardly into the annular flow passage 46 which extends rearward within the tubular outer member 11 as above described.

The rotatable elongate inner member 30 further includes a coaxial flexibly bendable portion 90 (FIG. 3) coaxially fixed at its opposite ends to the front end of the shaft front part 45F and to the rear end 74 of the head 71 for rotatably driving the head 71 from the shaft 44 and allowing the shaft 44 to axially press the nose 72 of the head 71 forwardly against the rounded front end 43 of the tubular outer member 11. This keeps the mouth 80 in axially correct position with the window 41 while yet allowing bending of the rotatable inner member 30, in the manner seen at FIG. 2, during rotation of the rotatable inner member, despite angling of the distal tip portion 14 with respect to the intermediate portion 15 of the tubular outer member 11 and without scuffing of the rotatable inner member 30 with respect to the surrounding angled portion 70 of the tubular outer member 11. As to the latter, the flexible bendable portion 90 is to be maintained, during rotation, coaxial with the generally curved surrounding angled portion 70 of the outer tubular member and hence so as to maintain a constant thickness annular space therebetween during rotation, as generally indicated in FIG. 2. Further, the member 90, while flexibly bendable during rotation is non-twistable so as to transmit the necessary rotational driving torque from the handpiece HP to the head 71.

In the preferred embodiment shown, the flexibly bendable portion 90 (FIG. 2) comprises an elongate flexible member 91 having a central part 92 located within the angled portion 70 of the tubular outer member 11 and wherein bending during rotation occurs to accommodate the angle of such angled portion 70. The flexible member 91 further includes elongate distal and proximal parts coaxially flanking the central part 92 and respectively extending coaxially into fixed coaxial driving engagement with the adjacent rear and front ends of the head 71 and shaft 44.

In the preferred embodiment shown, the flexible member 91 comprises length of conventional wound-wire flexible shafting. In one unit constructed according to the present invention, the flexible member 91 was a 0.070 inch diameter, 1.65 inch long piece of flexible shafting constructed of stainless steel wire, and available from Suhner Manufacturing Inc. of Rome, Ga. under part No. A-225-4784. That particular unit is shown in FIG. 3 wherein the flexible member 91 comprises a coaxial center wire 95, wound with a first layer of intermediate wound wires 96 (here four in number) in one circumferential direction, which first circumferential layer is then over wound with a second layer of outer wound wires 97 (here five in number). To prevent unwinding of the wires, the ends of the flexible member 91 are here fused by welding as generally indicated at 100. The intermediate and outer wires are tightly wound in a conventional manner.

The end portions of the distal and proximal parts 93 and 94 of the flexible member 91 are coaxially connected to the head 71 and shaft 44 preferably by snug coaxial reception in the rear end portion of the central bore 73 of the head 71 and in a forward facing cylindrical recess 101 (FIG. 3) in the front end of the shaft 44. Actual fixing of the thus inserted ends of the flexible member 91 can be in any conventional manner. It is convenient to crimp the surrounding front end portion of the shaft 44 tightly to the proximal end portion 94 of the flexible member 91 as indicated at 102 in FIG. 3. The same can be done with respect to the distal end portion 93 housed in the head 71 although adhesive bonding, welding or the like may be used instead.

In the preferred embodiment shown, the entire portion of the flexible member 91 between the shaft 44 and head 71 is preferably snugly covered by a relatively thin-walled sheath 103 (FIG. 3). The sheath 103 prevents particles in the suctioned flowable material from entering between the coils of the outer wire layer 96 as the flexible member 91 flexes during rotation. Thus, a solid particle entering between adjacent wire coils on the outside of the bend cannot interfere with contact between such coils on the inside of the bend, following 180° of shaft rotation. In addition, the sheath 103 can act as a buffer preventing direct contact between the outer wires 96 of the flexible member 91 and the inside wall of the angled portion 70 of the tubular outer member 11, in the highly unlikely event of a malfunction wherein the flexible member 91 displaces radially sufficient to brush against the inside surface of the outer tubular member.

In the embodiment shown, the sheath 103 is conveniently a length of conventional heat shrink tubing, preferably polyester heat shrink tubing. This material is relatively low friction material and is capable of shrinking almost half diameter upon application of modest heat thereto, so as to snugly grip the outside of the flexible member 91. The sheath covered flexible member 91 has an effective outside diameter no more than that of the shaft 44 and tail 75 of the head 71, so as to continue the annular passage 46 axially therepast and not impede rearward flow of flowable material from the surgical site therepast.

Applicant has found that the flexible member 91 (FIG. 2) will maintain its coaxial location within the angled portion 70 of the outer tubular member and hence maintain equal radial spacing therein during rotation in surgical use at substantial rotational speeds, for example as high as about 3,000 to 6,000 rpm, given that the head 71 is held forwardly against the front end 43 of the outer tubular member and with substantial axial extension of distal and proximal parts 93 and 94 of the flexible member axially beyond the angled portion 70 of the outer tubular member. In one unit constructed according to the invention, and as shown in FIG. 2, the distal and proximal parts 93 and 94 of the flexible member occupy the straight parts of the outer tubular member flanking the angled portion 70 and are each at least as long as the central part 92 of the flexible member. The central part 92 occupies the angled portion 70 of the outer tubular member and hence is the part called upon to flex during rotation. In other words, the flanking distal and proximal parts 93 and 94 need not flex and are at least as long as the flexing central part 92 which they flank. Further, the coaxially fixed engagement of the distal and proximal parts 93 and 94 of the flexible member 91 with the opposed ends of the head 71 and shaft 44, which are coaxially rotatable within their corresponding portions of the outer tubular member 11, maintain the distal and proximal parts 93 and 94 of the flexible member 91 coaxial within the outer tubular member during rotation.

OPERATION

The tool 10 is readily manufacturable as follows, for example. Following formation of hemispherical distal tip portion 14 and angled portion 70 of the outer tubular member 11, the base 12 is formed and fixed thereto. As to the rotatable inner member, the shaft 44 and head 71 are formed as shown and the hub 31 is formed and fixed on the rear end portion of the shaft 44. The coil compression spring 35 may at any time be inserted into the rear facing recess 34 in the rear end of the base 12. The outer wrapped wire layer 93 of the flexible central portion 92 of the flexible member 91 is loosely sleeved over with the tubular heat shrinkable sheath 103 and its ends are fixedly telescoped in the proposed ends of the shaft 44 and head 71. Thereafter, gentle heating of the shrink tube sheath 103 radially shrinks it to tightly grip the outer wire layer 93 of the flexible member 91 throughout its exposed length. The molded plastic bushings 50R and 50F are radially resiliently snapped onto the reduced diameter shaft portions 51 and 52 respectively so as to rotate freely and coaxially thereon.

Thereafter, the tool 10 can be assembled by insertion of the rotatable inner member 30, head 71 first, forwardly into the rear end of the tubular outer member 11. This telescoping insertion proceeds most easily with the window 41 and mouth 80 facing in the same circumferential direction, for example both facing up with the tool 10 horizontal.

During insertion of the rotatable inner member 30 into the tubular outer member 11, the chamfered forward ends of the bushings 50F, R slide axially therewith, in a low friction manner, forward into their positions shown in the tubular outer member 11 and the head 71 comes axially to press against the closed front end 43 of the outer tubular member 11. The flexible member 91, during such telescoping assembly, accommodates the curvature of the angled portion 70 of the outer tubular member since, while it is laterally bendable it is not axially compressible.

The tool 10 is rearwardly inserted into the chuck C of a handpiece HP in a conventional way, namely by telescoped insertion rearwardly thereinto of the drive hub 31 and outer member base 12. Upon completion of insertion, the split ring 23 and pin 22 of the chuck C axially and radially fix the outer tubular member 11 with respect to the handpiece HP, and the handpiece shaft SH and double pin DP respectively resiliently push forward the resilient inner member distal tip portion 40 against the closed front end 43 of the outer tubular member and insert into opposed notches 32 of the hub 31 to rotatably drive the rotatable inner member upon conventional actuation of the motor means of the handpiece.

To use the tool 10, chucked in a suitable handpiece HP, the handpiece is connected to a suitable power source P (e.g. electric power source) for electric motor MM, and normally to a suitable suction source S. The surgeon can then insert the distal tip portion 14 of the tool in a small, for example arthroscopic, incision into a surgical site in a patient, for example for arthroscopic trimming of the edge of the meniscus cartilage in a knee joint. The angling of the distal tip portion 14 with respect to the proximal portion of the tool 10 permits the surgeon to reach, and orient the cutting window 41 toward, portions of the surgical site which would not readily be accessible by a straight tool without applying excessive tilting or sideways forces to the tissue of the patient through which the tip of the tool is inserted, or without relocating the tool in a new incision.

Surgeon actuation of the handpiece motor MM rotates the rotatable inner member 30. The flexibly bendable portion 90 (FIG. 2) flexes as needed to maintain coaxiality with the angled portion 70 of the outer tubular member 11, i.e. to maintain its centered position therein shown in FIG. 2, during rotation of the inner member. The flexibly bendable portion 90 cannot straighten because of the axial compression force on the inner tubular member due to its axial entrapment between (1) the spring 35 and the drive shaft SH of the handpiece HP at the proximal end thereof and (2) the rounded, closed front end 43 of the outer tubular member at the distal end thereof. Rotation of the head 71 moves the cutting edges 42 of the inner member in a circumferential shearing manner with respect to the cutting edges defined by the window 41, so as to separate small bits of tissue sequentially from the intended portion of the surgical site.

Typically the surgical site is infused with irrigation liquid, from a suitable conventional source not shown. With the handpiece HP connecting the inner portion of the outer tubular member 11 to the suction source S (FIG. 2) excess irrigation liquid, with bits of tissue and other particulate matter entrained therein, is drawn from the surgical site through the window 41 and repetitively as the head 71 rotates, through the mouth 80 thereof, through the central bore 73 thereof and radially out the port 83 thereof and rearwardly along the annular suction passage 46 surrounding the rotating inner member 30. Such rearward flow is facilitated by the channels 55 between the lobes 56 of the bushings 50F, R and by the radial spacing of the rotatable inner member 30 from the interior wall of the tubular outer member 11. Such flow continues through the loose central opening 62 and radially outward opening windows 65 and troughs 66 of the hub 31 and through the suction passage (not shown) in the handpiece HP to the suction source. Such flow is indicated by the arrows in FIG. 2 and FIG. 3.

The tool 10 is constructed in a relatively inexpensive manner so as to be disposable after a single use (for example after a single surgical procedure), so as to avoid need for subsequent sterilization, the costs thereof, the risk of imperfect sterilization, and the resulting risk of contamination of a second patient by bodily materials of a first.

DESCRIPTION OF SECOND EMBODIMENT

FIGS. 13–24 show a further embodiment of the invention, which is substantially the same as that described above with respect to FIGS. 1–12 except as discussed below. Features of the FIGS. 1–24 embodiment similar to those of FIGS. 1–12, are identified by the same reference numerals with the suffix A added.

In this further (FIGS. 13–24) embodiment, the driven rotatable elongate inner member 30A extends coaxially and rotatably within the tubular outer member 11A, but is modified to further facilitate the removal of tissue along the length thereof.

More particularly, referring to FIG. 24, the flow path of removed tissue is modified as shown by the reference arrows in FIG. 24, to minimize restriction of flow.

The rotatable inner member 30A (FIG. 23) has a drive end portion 57A which is conventionally coaxially fixed in driven relation within an inner bore 110 of the hub 31A. The inner bore 110 extends rearwardly from the inner member 30A and opens into a transverse access bore 112 which communicates with the suction source S (not illustrated in FIGS. 23 and 24) to remove tissue from the inner member 30A.

Figure 22:
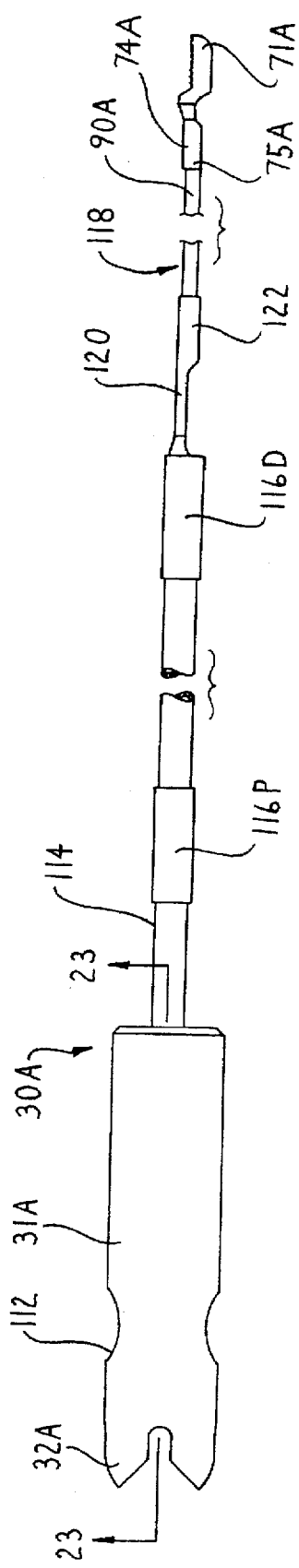
FIG. 22 is a broken front elevational view of the rotatable drive hub and inner member of the embodiment illustrated in FIG. 13.
Figure 23:
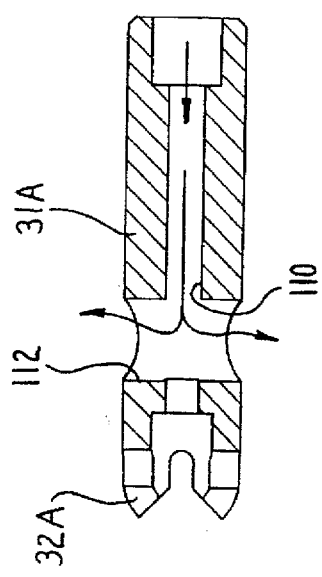
FIG. 23 is a central cross sectional view substantially taken on the line 23—23 of FIG. 22.

Referring to FIGS. 22 and 24, the inner member 30A includes a proximal portion 114 coaxially fixed to and extending forward from the hub 31A. The outside diameter of the portion 114, preferably, is only slightly smaller than the inside diameter of the sleeve 13A. The proximal portion 114 is supported for rotation within the hollow base 12A and the sleeve 13A of the tubular outer portion 11A by bearing sleeves 116 which are disposed about the outer peripheral surface of the inner member 30A. Although here shown thicker in the drawings, for convenience in illustration, preferably the bearing sleeves 116 are thin walled (e.g. approximately 0.001 in. thick) and formed of a shrink wrap polymer such as Teflon (TM) which during rotation reduces the friction occurring between the inner member 30A and the outer member 11A. Preferably, two bearing sleeves 116 are provided, i.e. a proximal bearing sleeve 116P which is disposed within the hollow base 12A during use and a distal bearing sleeve 116D which is disposed within the sleeve 13A away from the base 12A. The distal bearing sleeve 116D further serves the purpose of preventing undesirable entry of tissue between the inner member 30A and the sleeve 13A, as generally seen in FIG. 24.

The proximal portion 114 is provided with a tubular shape which defines an interior suction passage 46I through the interior and along the axial length thereof from a distal end and extending to a proximal end at the hub 31A. This interior suction passage 46I coaxially communicates with the inner bore 110 of the hub 31A.

Referring to FIG. 22, the inner member 30A also includes a distal portion 118 which connects to a transition portion 120 of the proximal portion 114. The distal portion 118 is similar to that previously described herein at 40, in that it includes a coaxial flexibly bendable portion 90A which has a radial clearance between the outside diameter thereof and an inside diameter of the sleeve 13A, as can be seen in FIG. 24. This radial clearance defines an annular suction passage 46A.

Referring to FIGS. 16 and 17, the transition portion 120 is formed integral with the proximal portion 114 and extends forwardly therefrom. To facilitate connection to the bendable portion 90A as well as facilitate the flow being received from the head 71A along the annular suction passage 46A, the transition portion 120 necks down from the increased diameter at the proximal portion 114 and reduces to a reduced diameter portion 122 which has an outside diameter proximate the outside diameter of the distal portion 118. To permit entry of tissue being removed from the surgical site, the transition portion 120 includes a lateral opening 124 which communicates with the interior of the proximal portion 114 and accordingly, communicates with the interior suction passage 46I thereof.

This opening 124 also communicates with the annular suction passage 46A adjacent thereto. Preferably the lateral opening 124 is elongate so as to provide a sufficiently sized opening to permit free access of tissue therein. In particular, as seen in FIG. 17, the opening 124 extends from the reduced diameter portion 122 and terminates proximate the maximum diameter of the proximal portion 114.

Referring to FIGS. 13 and 14, the transition portion 120 terminates forwardly at an entry opening 126 which is adapted to coaxially receive the proximal end 94A of the bendable portion 90A in tight-fitting engagement. To further secure the bendable portion 90A within the entry opening 126, the bendable portion 90A may be permanently affixed by such conventional techniques as welding or brazing or staking.

Forwardly of the transition portion 120 the distal portion 118, and more particularly, the bendable portion 90A thereof is formed substantially identical to that of the previous embodiment described herein. As illustrated in FIG. 24, the distal portion 118 has a reduced diameter in comparison to the inner diameter of the outer member 11A, such that the annular suction passage 46A is formed between the outer surface 136 of the distal portion 118 and the inner surface 138 of the sleeve 13A of the outer member 11A. With the lateral opening 124 provided in the transition portion 120, the tissue flows along the annular suction passage 46A and into the interior suction passage 46I of the proximal portion 114. Similar to the first embodiment hereof, the bendable portion 90A has a distal end 93A which terminates proximate the distal tip portion 14A of the outer member 11A and is coaxially secured to the rear end 74A of the tissue working head 71A.

Referring to FIGS. 18–21, the head 71A includes a central bore 73A, a reduced diameter tubular tail 75A, cutting edges 42A and a transverse, chordal flow port 83A. The head 71A also includes means for working tissue having an upward opening mouth 80A.

As in the previous embodiment, a path for fluent material is provided through the head 71A from the mouth 80A through the central bore 73A and out through the flow port 83A. To facilitate flow therethrough, the flow port 83A is modified so as to taper forwardly and terminate at a distal edge 140 thereof which increases the size of the port 83A. This distal edge 140 is disposed substantially diametrically opposite a proximal edge 142 of the tissue working cutting edges 42A. By providing the distal edge 140 substantially opposite the proximal edge 142 opposite thereto a substantially diagonal flow path results between the cutting edges 42A and the flow port 83A which provides an improved flow of the tissue being removed. This improved flow avoids unnecessary contact with the walls of the head 71A which can impede flow. This arrangement provides an increased opening size for the flow port 83A which further facilitates flow of fluent material therefrom.

In addition, the radial bearing portion 76A of the head 71A is provided with a thinner wall thickness and the interior surface of the central bore 73A is shaped so as to taper rearwardly to the reduced diameter tail 75A thereof. This tapering arrangement provides the proximal edge 142 with a reduced cross-sectional area and provides a sloping surface in the central bore 73A which further facilitates flow therethrough. In other words, this maximizes the size of the central bore 73A in the region of the distal edge 140 and the proximal edge 142.

This tapering of the interior surface of the head 71A preferably is accomplished by forming the head 71A with a tubular shape having a uniform diameter. Then, the distal end 74A is swaged to form the reduced diameter tail portion 75A.

Referring to FIGS. 15 and 21, flow is further promoted by providing the tail portion 75A with a C-shaped cross section which is accomplished by cutting off a bottom section of the tail 75A which thereby provides an opening which communicates with the annular suction passage 46A as illustrated in FIG. 24. The tail portion 75A receives and is coaxially fixedly secured to the distal end 93A of the bendable portion 90A. By providing a C-shaped cross section for the tail 75A, the width of the annular suction passage 46A in the area of the opening of the C-shape is maximized to thereby maximize the flow of tissue material therealong.

The distal end of the bendable portion 90A is sufficiently secured by providing the tail 75A with this C-shaped arcuate section of sufficient size so that the bendable portion 90A may not be dislodged through the opening of the tail 75A. The bendable portion 90A is further secured therein by such securing techniques as welding or brazing.

During operation, the inner member 30A of this embodiment is operated substantially as described herein with respect to the aforesaid embodiment. Flow, however, is improved from the head 71A to the hub 3A by the arrangement described herein. In particular, tissue flows through the central bore 73A, out of the flow port 83A, along the annular suction passage 46A disposed about the bendable portion 90A until reaching the transition portion 120. At the transition portion 120, the tissue will flow through the lateral opening 124 and thereafter through the interior suction passage 46A of the proximal portion 114. With this flow arrangement, obstruction of the tissue as it flows along the suction path is minimized.

Although particular preferred embodiments of the invention have been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A powered rotatable surgical tissue working tool for chucking in a powered rotating surgical handpiece, comprising:

a tubular outer member having a proximal end portion fixable in a handpiece and having a hollow distal tip portion with an opening thereinto;

a rotatable inner shaft extending coaxially within and rotatable inside said outer member and having at least a tubular proximal portion having an inner surface defining an interior suction passage and at least a distal portion radially spaced from the inside surface of said tubular outer member by an annular suction passage, said distal portion including flow blocking means for blocking tissue flow through the central portion of said distal portion, said proximal portion having a cross-section reducing transition portion at a distal end thereof connecting said distal portion and said proximal portion, said transition portion having a transition opening in communication with said interior suction passage and said annular suction passage;

a tissue working head rotatably drivable by and fixed with respect to a distal end of said inner shaft, said head being rotatable inside said hollow distal tip portion of said tubular outer member, said head comprising surgical tissue working means at the distal end thereof cooperable with said opening in said distal tip portion of said outer member for engaging and removing tissue from a surgical site during surgery, said head further comprising a lateral port opening between said tissue working means and said annular suction passage in said outer tubular member, said head having a reduced radius tail disposed proximally of said port for continuing said annular suction passage forward along said tail to said port.

2. The apparatus according to claim 1, wherein said proximal portion includes bearing means for substantially coaxially rotatably supporting said proximal portion of said inner shaft within said outer member, said bearing means disposed sealingly between said proximal portion and said outer member and proximate said transition opening.

3. The apparatus according to claim 1, in which said distal portion of said inner shaft is a flexibly bendable member fixed at its ends to and between said transition portion and said head to rotatably drive said head from said inner shaft, said tubular outer member having an angled portion for angling said hollow distal tip portion with respect to an intermediate portion of said tubular outer member, said flexibly bendable member being located in said angled portion of said outer tubular member.

4. The apparatus according to claim 3, in which said flexibly bendable member comprises a substantially non-twistable torque transmitting member, said transition portion and head having coaxial, opposed entries fixedly receiving therein the proximal and distal ends, respectively, of said flexibly bendable member, for transmitting torque from said proximal portion of said inner shaft through said flexibly bendable member thereof to said head.

5. The apparatus according to claim 4, wherein said reduced radius tail defines said entry for receiving the distal end of the flexibly bendable member, said reduced radius tail having a C-shaped cross sectional shape which opens laterally into said annular suction passage and adjacent said lateral port opening of said head.

6. The apparatus according to claim 3, wherein said flexibly bendable member is a coaxial cable.

7. The apparatus according to claim 1, in which the head is substantially bullet shaped but has a central bore extending forwardly through its proximal end and ending adjacent its distal end, the distal portion of said head being relieved to define said surgical tissue working means and to communicate same with the forward end of said central bore, said distal portion of said inner shaft being a flexibly bendable member, the distal end of said flexibly bendable member being fixed within the proximal end portion of said central bore, said lateral port being in a mid-length portion of said head ahead of said flexibly bendable member end and communicating between said bore proximal end and the interior of said tubular outer member adjacent said surgical material working means, said bore and port defining a suction passage in said head in communication with said annular suction passage.

8. The apparatus according to claim 7, wherein said surgical tissue working means includes an opening in communication with said central bore and which defines a proximal edge thereof and said lateral port opening defines a distal edge thereof, said proximal edge and said distal edge being disposed substantially diametrically opposite one with the other to facilitate flow of tissue from said surgical site through said central bore and out of said lateral port.

9. The apparatus according to claim 7, wherein said surgical tissue working means includes an opening in communication with said central bore and which defines a proximal edge thereof, an interior surface of said central bore tapering radially inwards away from said proximal edge and toward the reduced radius tail portion to facilitate flow thereat.

10. The apparatus according to claim 1, wherein said flow blocking means comprise first and second opposite end portions which are enclosed for said blocking of the tissue flow through the central portion.

11. The apparatus according to claim 1, wherein said flow blocking means comprise an imperforate outer peripheral surface of said distal portion, said annular suction passage being defined between said outer peripheral surface and said inside surface of said outer tubular member.

12. The apparatus according to claim 1, wherein at least one of said transition opening and said lateral port opening is larger than the cross-sectional area of said annular suction passage.

13. The apparatus according to claim 12, wherein said tissue working tool includes only one said transition opening and only one said lateral port opening.

14. A powered rotatable surgical tissue working tool for chucking in a powered rotating surgical handpiece, comprising:
an elongate tubular outer member having a proximal end portion fixable in a handpiece and having a hollow distal tip portion with an opening thereinto;
an elongate rotatable inner shaft extending coaxially within and rotatable inside said outer member and having at least a distal portion radially spaced from the inside surface of said tubular outer member by an elongate annular suction passage, said distal portion including a flexibly bendable member having flow blocking means for blocking tissue flow through the central portion of said flexibly bendable member; and
a tissue working head rotatably drivable by and fixed with respect to a distal end of said inner shaft, said head being rotatable inside said hollow distal tip portion of said outer member, said head comprising surgical tissue working means at the distal end thereof cooperable with said opening in said distal tip portion of said outer member for engaging and removing tissue from a surgical site during surgery, said head further comprising a lateral port opening between said tissue working means and said annular suction passage, said head having a reduced radius tail proximally of said port for continuing said annular suction passage of said outer tubular member forward along said tail to said port, said head having a central bore extending forwardly through its proximal end and ending adjacent its distal end and which fixedly receives the distal end of said flexibly bendable member within the proximal end thereof, the distal portion of said head being relieved to define an opening of said surgical tissue working means, the last mentioned opening having a proximal edge and communicating with said central bore, said central bore having an interior surface tapering radially inwards away from said proximal edge of said opening of said tissue working means and toward the reduced radius tail portion to facilitate flow of tissue into said central bore.

15. The apparatus according to claim 14, in which said elongate rotatable inner shaft includes a tubular proximal portion having an inner surface defining an interior suction passage, said proximal portion having a tapered transition portion connecting said distal portion and said proximal portion coaxially together, said transition portion having an opening in communication with said interior suction passage and said annular suction passage.

16. The apparatus according to claim 15, wherein said flexibly bendable member is fixed at its ends to and between said transition portion and said head to rotatably drive said head from said distal portion said outer tubular member having an angled portion for angling said hollow distal tip portion with respect to an intermediate portion of said tubular outer member, said flexibly bendable member being located in said angled portion of said outer tubular member.

17. The apparatus according to claim 16, in which said angled portion of said outer tube and said flexible member have substantially the same center of curvature.

18. The apparatus according to claim 14, in which said head defines an entry proximate said reduced radius end which fixedly receives therein the proximal end of said flexibly bendable member for transmitting torque from said proximal portion through said flexible member to said head, said reduced radius end having a C-shaped cross section which opens laterally into said annular suction passage and coaxially adjacent said lateral port opening of said head.

19. The apparatus according to claim 14, wherein said surgical tissue working means includes an opening in communication with said central bore, the last mentioned opening having a proximal edge, said lateral port opening having a distal edge, said proximal edge and said distal edge being disposed substantially diametrically opposite one with the other to facilitate flow of tissue from said surgical site through said central bore and out of said lateral port.

20. A powered rotatable surgical tissue working tool for chucking in a powered rotating surgical handpiece, comprising:
an elongate tubular outer member having a proximal end portion fixable in a handpiece and having a hollow distal tip portion with an opening thereinto;
an elongate rotatable inner shaft extending coaxially within and rotatable inside said outer member and having at least a distal portion radially spaced from the inside surface of said tubular outer member by an elongate annular suction passage, said distal portion having flow blocking means for blocking tissue flow through the central portion of said distal portion;
a hollow tissue working head having a hollow interior and being rotatably drivable by and fixed with respect to a distal end of said inner shaft, said head being rotatable inside said hollow distal tip portion of said outer member, said head comprising surgical tissue working means at the distal end thereof cooperable with said opening in said distal tip portion of said outer member for engaging and removing tissue to the interior of the hollow head from a surgical site during surgery, said surgical tissue working means having a proximal edge, said head further comprising a lateral port opening radially between said head hollow interior, which defines a central bore thereof, and said annular suction passage in said outer member, said lateral port defining a distal edge which is substantially diametrically opposite said proximal edge of said surgical tissue working means, said head having a reduced radius tail extending toward said shaft and disposed proximally of said port for continuing said annular suction passage of said outer tubular member forward along said tail to said port, said reduced radius tail defining an entry for receiving a distal end of said distal portion and having a C-shaped cross section to maintain the radial width of said annular suction passage therealong.

21. The apparatus according to claim 20, wherein said central bore has an interior surface tapering radial inwards away from said proximal edge of said opening of said tissue working means and toward the reduced radius tail portion to facilitate flow of tissue into said central bore.

22. The apparatus according to claim 21, in which said elongate rotatable inner shaft includes a tubular proximal portion having an inner surface defining an interior suction passage, said proximal portion having a tapered transition portion connecting said distal portion and said proximal portion coaxially together, said transition portion having an opening in communication with said interior suction passage and said annular suction passage.

23. The apparatus according to claim 22, in which said proximal portion of said inner shaft is a flexibly bendable member fixed at its ends to and between said transition portion and said head to rotatably drive said head from said inner shaft, said tubular outer member having an angled portion for angling said hollow distal tip portion with respect to an intermediate portion of said tubular outer member, said flexibly bendable member being located in said angled portion of said outer tubular member.

24. The apparatus according to claim 23, in which said head defines an entry proximate said reduced radius end which fixedly receives therein the proximal end of said flexibly bendable member for transmitting torque from said proximal portion through said flexible member to said head, said reduced radius end having a C-shaped cross section which opens laterally into said annular suction passage and coaxially adjacent said lateral port opening of said head.

* * * * *

UNITED STATES PATENT AND TRADEMARK OFFICE
CERTIFICATE OF CORRECTION

PATENT NO. : 5,690,660  
DATED : November 25, 1997  
INVENTOR(S) : Barry J. KAUKER, et al.

It is certified that error appears in the above-indentified patent and that said Letters Patent is hereby corrected as shown below:

On the title page, item [63], third line change "1991" to ---1994---.

Signed and Sealed this

Twenty-seventh Day of October, 1998

Attest:

BRUCE LEHMAN

*Attesting Officer*       *Commissioner of Patents and Trademarks*